United States Patent [19]

Vorbruggen

[11] 4,082,911
[45] Apr. 4, 1978

[54] PROCESS FOR THE PREPARATION OF NUCLEOSIDES

[75] Inventor: Helmut Vorbruggen, Berlin, Germany

[73] Assignee: Schering Aktiengesellschaft, Berlin and Bergkamen, Germany

[21] Appl. No.: 660,675

[22] Filed: Feb. 23, 1976

[30] Foreign Application Priority Data

Feb. 24, 1975 Germany ................ 2508312

[51] Int. Cl.$^2$ ............... C07H 19/06; C07H 19/16
[52] U.S. Cl. ............................... 536/23; 536/24; 536/26; 424/180
[58] Field of Search ............... 536/23, 24, 26

[56] References Cited

U.S. PATENT DOCUMENTS

| 3,352,849 | 11/1967 | Shen et al. ................ 536/23 |
| 3,354,160 | 11/1967 | Duschinsky et al. ........ 536/23 |
| 3,748,320 | 7/1973 | Vorbruggen et al. ........ 536/23 |
| 3,891,623 | 6/1975 | Vorbruggen et al. ........ 536/23 |

*Primary Examiner*—Johnnie R. Brown
*Attorney, Agent, or Firm*—Millen & White

[57] ABSTRACT

The use of trialkylsilyl ester catalysts in place of Lewis acid or Friedel-Crafts catalysts in nucleoside synthesis gives increased yields and a simplified working-up process for recovering the nucleoside product.

11 Claims, No Drawings

PROCESS FOR THE PREPARATION OF NUCLEOSIDES

BACKGROUND OF THE INVENTION

Various processes for the preparation of nucleosides are known per se. For example, Y. Furukawa et al in Chem. Pharm. Bull. 16:1067 (1968) described the reaction of purines with 1-O-acyl or 1-O-alkyl derivatives of a sugar in the presence of Friedel-Crafts catalysts to obtain the corresponding N-glycosides. German Pat. No. 1,919,307 discloses a process for the production of nucleosides in which silylated N-heterocyclic bases are reacted with masked 1-halo-, 1-O-alkyl-, and especially 1-acyl-sugars in the presence of Friedel-Crafts catalysts. Technical scale application of such conventional processes can be complicated because the separation of the salts of the Lewis acids and/or Friedel-Crafts catalysts formed during the reaction frequently causes difficulties in working-up the reaction mixtures and additional chemical operations thus become necessary. These disadvantages also manifest themselves in a reduced yield of the finally desired product.

OBJECTS OF THE INVENTION

Accordingly, it is a general object of this invention to provide an improved process for nucleoside synthesis.

Another object of this invention is to provide such a process wherein the formation of unwanted emulsions or colloids is avoided while working-up the reaction mixture.

A further object of this invention is to provide such a process wherein the product is principally a β-glycoside obtained in a high yield.

Upon study of the specification and appended claims, further objects and advantages of this invention will become apparent to those skilled in the art.

SUMMARY OF THE INVENTION

Briefly, these objects and advantages are attained in one aspect of the present invention by providing, in a process for preparing a nucleoside by catalytically reacting a silylated nucleoside organic base with a 1-O-acyl, 1-O-alkyl or 1-halo derivative of a masked nucleoside sugar to form a nucleoside of said base and said sugar, the improvement which comprises:

employing a catalyst consisting essentially of a trialkylsilyl ester of an esterifiable mineral acid or of a strong organic acid, said acid having a $-H_o$ value of a least 12.00 [R. J. Gillespie et al., J.Amer.Chem.Soc. 95, 5173(1973)], whereby a reaction product is formed containing principally the β-derivative of said sugar.

DETAILED DISCUSSION

It has now been found that the prior art Friedel-Crafts catalysts, e.g. $SnCl_4$, can be replaced by trialkylsilyl esters, preferably the trimethylsilyl esters, of mineral acids, e.g. perchloric acid or fluorsulfonic acid, or of strong organic acids, e.g. trifluoromethanesulfonic acid, etc., as the catalysts.

The trialkylsilyl portion of the ester is one in which the alkyl groups are all lower alkyl of 1-6 carbon atoms, preferably methyl or ethyl and especially methyl. The alkyl groups may each be the same or different, although it is preferred that at least one, preferably two and especially all three, alkyl groups are methyl or ethyl. Especially suitable are the easily available mono- or polytrimethylsilyl esters, e.g. $(CH_3)_3Si—OClO_3$, $(CH_3)_3Si—OSO_2F$ and $(CH_3)_3Si—OCOCF_3$.

The esterified mineral acid or organic acid is a strong acid, i.e. one having a $—H_o$ value of at least 12.00, and is capable of trialkylsilyl ester formation. Suitable such acids are well known in the art and include but are not limited to the halogenated per-acids, e.g. perfluoric and perchloric acids; sulfur-containing acids, e.g. fluoro- and chloro- sulfonic acids, sulfuric and sulfonic acids; and strong organic acids, e.g. trifluoromethane sulfonic acid. By replacing, e.g. $SnCl_4$ as catalyst by the trimethylsilyl esters of acids in nucleoside synthesis, different donor acceptor or τ-complexes are formed between the silylated heterocycles as bases or donors and the trimethylsilylesters of strong acids compared to catalysts like $SnCl_4$, since $SnCl_4$ or $TiCl_4$ have the coordination number of 6 whereas the trimethylsilylesters of strong acids form probably only simple acid-base donor-acceptor complexes. Since these complexes determine whether silylated uracils form the natural $N_1$-nucleoside or the biologically inactive $N_3$-nucleosides, the new catalysts give a much higher proportion of the desired $N_1$-nucleosides (e.g. examples 7-12) than $SnCl_4$ or $TiCl_4$. Furthermore the adverse formation of emulsions and colloids during the working-up process is avoided and the yields are increased.

This invention accordingly relates to a process for the preparation of preferably heterocyclic nucleosides by reacting the corresponding silylated, preferably heterocyclic organic nucleoside bases with a 1-O-acyl, 1-O-alkyl or 1-halogen derivative of a masked sugar in the presence of a catalyst, characterized in that trialkylsilyl esters, especially trimethylsilyl esters, of mineral acids or strong organic acids are utilized as the catalyst.

In principle, all silylated organic bases useful in nucleoside synthesis are suitable for use with the catalysts of the present invention. Such bases are well known in the art and include but are not limited to organic bases of the Formulae

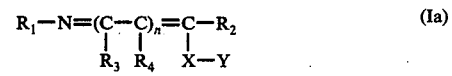     (Ia)

or

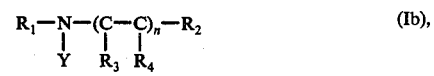     (Ib), wherein

X is oxygen or sulfur;

n is the number 0 or 1; and $R_1$ and $R_2$ are each a saturated or unsaturated optionally substituted aliphatic, cycloaliphatic or aromatic residue of a nucleoside base, or $R_1$ and $R_2$ together represent a bivalent aliphatic residue which can contain one or two nitrogen atoms, and $R_3$ and $R_4$ are each hydrogen, lower alkyl, lower alkoxycarbonyl or lower alkylaminocarbonyl, or $R_3$ and $R_4$ together represent the bivalent residues

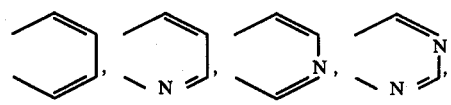

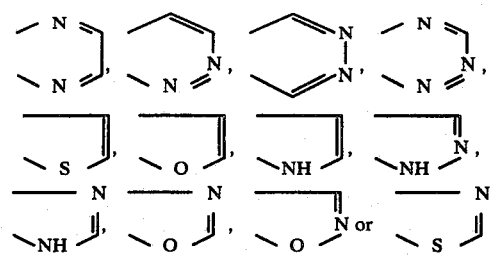

which can be substituted in the usual manner, and Y is trialkylsilyl of 1-6 carbon atoms in each alkyl group, especially trimethylsilyl.

Preferred values for $R_1$ and $R_2$ as aliphatic are the lower alkyl groups, preferably of 1-4 carbon atoms, i.e. methyl, ethyl, propyl or butyl. Preferred values for $R_1$ and $R_2$ as aromatic are aryl and aralkyl, e.g. phenyl, benzyl, tolyl, xylyl, etc.

The bivalent residues $R_1$ and $R_2$ or $R_3$ and $R_4$ can contain the following substituents, for example: lower alkyl, trifluoromethyl, alkanoyl, hydroxy, alkoxy, alkanoyloxy, carboxyl, carboxamide, alkoxycarbonyl, dialkylaminocarbonyl, amino, nitro, nitriloxo or halogen.

Preferred starting compounds are those silylated organic bases wherein $R_1$ and $R_2$ are linked to a ring, especially in such a way that the heterocyclic bases contain five or six atoms in the ring, and among those one to three nitrogen atoms.

The silylated organic bases according to Formulae Ia and Ib are preferably derived from the following heterocyclic bases: uracil, cytosine, 6-azauracil, 2-thio-6-azauracil, thymine, N-acetyladenine, guanine, lumazine [2,4(1H,3H) pteridinedione], imidazole, pyrazine, thiazole or triazole, each of which can optionally be substituted by one or more of the aforementioned residues $R_1$ and $R_2$ as well as $R_3$ and $R_4$.

In case $R_1$ and $R_2$ are linked together in a ring, the bivalent residue $R_1$ and $R_2$ represents, in particular:

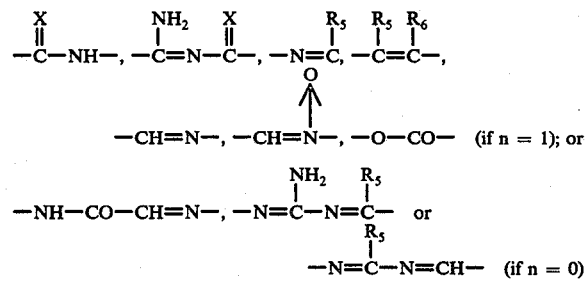

wherein

X has the above-indicated values and $R_5$ and $R_6$ each represent hydrogen, alkyl, alkoxycarbonyl, or alkylaminocarbonyl.

The sugar derivatives utilized in accordance with this process are derived preferably from ribose, deoxyribose, arabinose and glucose.

All free hydroxy groups of the sugars are suitably blocked or masked in a conventional manner. Suitable sugar blocking groups are those customary in sugar chemistry, e.g. alkanoyl, benzoyl, p-chlorobenzoyl, p-nitrobenzoyl, p-toluyl, benzyl, etc. The nature of the masking group is not critical, since this portion of the molecule is inert with respect to the present reaction.

When the nucleosides to be prepared in accordance with this process contain O-acyl-blocked sugar residues, it is possible to use, inter alia, in addition to the already mentioned blocking groups, the blocking groups of the following acids: propionic acid, butyric acid, valeric acid, caproic acid, enanthic acid, undecylic acid, oleic acid, pivalic acid, cyclopentylpropionic acid, phenylacetic acid and adamantanecarboxylic acid.

In the nucleosides obtained according to this process, the free or blocked sugar residue is preferably linked to the nitrogen atom in the manner of a β-glycoside.

The process of the present invention is generally applicable for the production of nucleosides. Preferred products of the process are nucleosides of the general Formula II

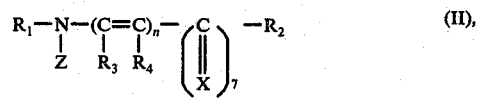

wherein $R_1$, $R_2$, $R_3$, $R_4$, X and $n$ have the above-indicated values;

Z is a free or blocked sugar residue; and m is the number 0 or 1.

The nucleosides producible in accordance with this process and, in particular, the products of Formula II, are biologically active, as is well known in the art. Depending upon the specific solubility, they can be administered, depending on the choice of the substituent, either systematically as an aqueous or alcoholic solution or locally as an ointment or a jelly.

The various nucleosides exhibit valuable pharmaceutical properties, depending on the individual compound, e.g. enzyme-inhibiting, antibacterial, antiviral, cytostatic, antipsoriatic and anti-inflammatory activities.

The reaction of the silylated organic bases, e.g. the bases of Formula Ia or Ib, with a 1-O-acyl, 1-O-alkyl or 1-halogen derivative of a blocked sugar in the presence of the catalyst according to this invention takes place in a suitable inert, preferably aprotic, solvent, e.g. methylene chloride, chloroform, carbon tetrachloride, benzene, toluene, acetonitrile, ethylene chloride, ethylene dichloride, dioxane, tetrahydrofuran, dimethylformamide, carbon disulfide, chlorobenzene, sulfolane, molten dimethylsulfone, etc.

The reaction can be conducted at room temperature or higher and/or lower temperatures, generally at 0°–100° C., preferably at 0°–20° C. The reactants are generally used in the reaction in an approximately equimolar amount, but the silylated heterocyclic is frequently utilized in a minor excess to obtain a maximally quantitative conversion of the sugar component. 0.1 equivalent of the catalyst is generally a sufficient catalytic amount but employing equivalent amounts of catalyst permit the reaction to be conducted at the lower temperature of 0°–20°, affording often higher yields of the desired $N_1$-nucleoside.

The catalysts utilized herein have a great advantage over the earlier used Lewis acids or Friedel-Crafts catalysts in that they can be removed immediately and quantitatively simply by shaking with bicarbonate solution, without the formation of emulsions or colloids, because they are at once hydrolyzed to the salt and hexamethyldisiloxane (b.p. 98° C.) which is removed during the evaporation of the solvents.

The catalysts can be prepared in accordance with methods known from the literature, for example from AgClO$_4$ with (CH$_3$)$_3$SiCl + (CH$_3$)$_3$Si—OClO$_3$ + AgCl as described by U. Wannagat and W. Liehr, "Angew. Chemie" [Applied Chemistry] 69:783 (1957) or, e.g. as in the case of the trimethylsilyl ester of trifluoromethanesulfonic acid, readily from CF$_3$SO$_3$H and (CH$_3$)$_3$SiCl as described by H. C. Marsmann and H. G. Horn in "Z. Naturforschung" [Journal of Biology] B27:4448 (1972) either with the use of a neutral solvent, such as benzene, or 1,2-dichlorethane or without any solvent. Filtration with the exclusion of moisture of salts which may have been formed leads to stable solutions of the silyl ester catalysts.

From acylated 1-O-alkyl and 1-O-acyl sugars, a sugar cation is produced during the reaction as a mineral acid salt, as well as the silylated O-alkyl and O-acyl derivative, respectively. The sugar salt reacts with silylated pyrimidine under nucleoside formation and renewed production of silyl ester of the mineral acid, so that catalytic amounts of the silyl ester of the mineral acid are often sufficient; if not, equivalent amounts of catalyst are used to conduct the reaction at lower temperature.

The yields of the novel reactions are higher than in the processes known heretofore; moreover, primarily β-derivatives of the sugars are obtained, while the undesired α-anomers are formed with the exception 2-desoxyribose only in subordinate amounts (less than 1% of the total product) or none at all.

Furthermore, the new catalysts give rise to much larger amounts of the desired natural N$_1$-nucleosides and only limited amounts of the undesired N$_3$-nucleosides e.g. in reaction with silylated uracils compared to SnCl$_4$ as catalyst.

To produce the known target compounds with free hydroxy groups, the blocking groups can then be removed in the usual way, e.g. by means of alcoholic solutions of ammonia or alcoholates, aqueous or alcoholic alkali, as well as, in case of the benzyl ethers, by reduction or hydrogenation.

The following examples serve for further explaining the process of this invention.

Without further elaboration, it is believed that one skilled in the art can, using the preceding description, utilize the present invention to its fullest extent. The following preferred specific embodiments are, therefore, to be construed as merely illustrative and not limitative of the disclosure in any way whatsoever. In the following Examples, the temperatures are set forth uncorrected in degrees Celsius; unless otherwise indicated, all parts and percentages are by weight.

EXAMPLE 1

5.15 millimoles of 2,4-bis(trimethylsilyloxy)pyrimidine and 5 millimoles of 1-O-acetyl-2,3,5-tri-O-benzoyl-β-D-ribofuranose were combined, in 20 ml. of 1,2-dichloroethane, with 2.5 millimoles of (CH$_3$)$_3$Si—O—ClO$_3$ in 20 ml. of benzene and allowed to stand for 1 week at 24° C. After the addition of 50 ml. of CHCl$_3$, the reaction mixture was shaken with 50 ml. of ice-cold saturated NaHCO$_3$ solution, a separating step was conducted, and the aqueous phase was furthermore shaken with a small amount of CHCl$_3$. After drying (Na$_2$SO$_4$) and evaporation, 2.8 g. of a crude product was thus obtained yielding, during recrystallization from 40 ml. of C$_6$H$_6$, 2.1 g. (75.5%) of pure uridine-2',3',5'-tri-O-benzoate; m.p. 138°–140° C.

EXAMPLE 2

The procedure of Example 1 was followed, except that only 0.5 mmole of (CH$_3$)$_3$SiOClO$_3$ (in 5 ml. of C$_6$H$_6$) was added thereto, and the mixture was refluxed for 4 hours under argon at a bath temperature of 100° C. The reaction mixture was worked up and crystallized, thus obtaining 2.238 g. (80.4%) of uridine-2',3',5'-tri-O-benzoate.

EXAMPLE 3

10 mmoles of 3-trimethylsilylthio-5-trimethylsilyloxy-1,2,4-triazine and 10 mmoles of β-glucose pentaacetate in 25 ml. of 1,2-dichloroethane were combined with 1 mmole of trimethylsilyl perchlorate in 7 ml. of C$_6$H$_6$. The mixture was refluxed for 3 hours at a bath temperature of 100° C. After the reaction mixture had been worked up as set forth in Example 1, 3.5 g. of a crude product was obtained, yielding, from ethanol, 3 g. (65%) of 2-(2,3,4,6-tetra-O-acetyl-β-D-glucopyranosyl)-3-thio-2,3,4,5-tetrahydro-1,2,4-triazin-5-one, m.p. 226° C.

EXAMPLE 4

5 mmoles of 2-trimethylsilyloxypyridine and 5 mmoles of 1-O-acetyl-2,3,5-tri-O-benzoyl-β-D-ribofuranose were combined, in 25 ml. of 1,2-dichloroethane, with 0.5 mmole of trimethylsilyl trifluoromethane sulfonate in 1 ml. of C$_6$H$_6$ and refluxed for 1.5 hours at a bath temperature of 100° C. and then worked up as usual. Crystallization of the thus-produced residue (2.8 g.) from 75 ml. of CCl$_4$ yielded 2.28 g. (85%) of 1-(2,3,5-tri-O-benzoyl-β-D-ribofuranosyl)-1,2-dihydropyridin-2-one, m.p. 140° C.

EXAMPLE 5

10 mmoles of 2-O-trimethylsilyloxy-4-trimethylsilylaminopyrimidine and 10 mmoles of 1-O-acetyl-2,3,5-tri-O-benzoyl-β-D-ribofuranose were combined, in 35 ml. of 1,2-dichloroethane, with 12 mmoles of (CH$_3$)$_3$SiO—SO$_2$CF$_3$ in 24 ml. of C$_6$H$_6$ and heated for one hour at 100° C. Working up the reaction mixture as described in Example 1 resulted in 3.869 g. (85%) of amorphous cytidine-2',3',5'-tri-O-benzoate.

EXAMPLE 6

10 mmoles of 6-benzoyltrimethylsilylamino-9-trimethylsilylpurine and 10 mmoles of 1-O-acetyl-2,3,5-tri-O-benzoyl-β-D-ribofuranose were combined, in 35 ml. of 1,2-dichloroethane, with 1 mmole of (CH$_3$)$_3$Si—O—ClO$_3$ in 7 ml. of C$_6$H$_6$. After 12 hours at a bath temperature of 100° C. and after working up the reaction mixture as disclosed in Example 1, amorphous adenosine tetrabenzoate was obtained which was saponified with 250 ml. of methanolic ammonia for 16 hours at 22° C. Evaporation and extraction with CH$_2$Cl$_2$ yielded, from methanol-H$_2$O, 2.3 g. (86.4%) of pure adenosine, m.p. 230°–232° C.

EXAMPLE 7

40 mmoles of 2,4-bis(trimethylsilyloxy)lumazine and 40 mmoles of 1-O-acetyl-2,3,5-tri-O-benzoyl-β-D-ribofuranose were combined, in 75 ml. of 1,2-dichloroethane, with 4 mmoles of (CH$_3$)$_3$Si—O—ClO$_3$ in 20 ml. of C$_6$H$_6$ and refluxed for 4 hours at a bath temperature of 100° C. After working up the mixture as usual, 20.2 g. (84%) of 1-(2,3,5-tri-O-benzoyl-β-D-ribofuranosyl)-lumazine was obtained. Using 12 mmoles of (CH$_3$)$_3$Si- —O—SO₂CF₃ at 24° C., a practically quantitative yield of the lumazine riboside was obtained.

EXAMPLE 8

55 mmoles of 1-trimethylsilyl-3-carboxymethyl-1,2,4-triazole and 55 mmoles of 1-O-acetyl-2,3,5-tri-O-benzoyl-β-D-ribofuranose were combined, in 100 ml. of 1,2-dichloroethane, with 5 mmoles of (CH₃)₃Si—O—SO₂CF₃ in 20 ml. of C₆H₆ and refluxed for 4 hours at a bath temperature of 100° C. After working up the mixture as usual, 24 g. (85.5%) of 1-(2,3,5-tri-O-benzoyl-β-D-ribofuranosyl)-3-carboxymethyl-1,2,4-triazole was produced.

EXAMPLE 9

10 mmoles of 2,4-bis(trimethylsilyloxy)-5-morpholinopyrimidine and 10 mmoles of 1-O-acetyl-2,3,5-tri-O-benzoyl-β-D-ribofuranose were combined, in 35 ml. of 1,2-dichloroethane, with 11 mmoles of (CH₃)₃Si-O—SO₂CF₃ in 20 ml. of C₆H₆ and stirred under argon for 20 hours at room temperature. The mixture was worked up as described in Example 1, yielding 6.36 g. (99%) of amorphous 5-morpholinouridine-2',3',5'-tri-O-benzoate.

EXAMPLE 10

11 mmoles of 2,4-bis(trimethylsilyloxy)-5-methoxypyrimidine and 12 mmoles of (CH₃)₃SiO—SO₂CF₃, dissolved in absolute 1,2-dichloroethane, were added to 5.04 g. (10 mmoles) of 1-O-acetyl-2,3,5-tri-O-benzoyl-β-D-ribofuranose in 75 ml. of 1,2-dichloroethane and agitated for 4 hours at room temperature. The mixture was worked up as described in Example 1, yielding from ethyl acetate/hexane 5.24 g. (98.3%) of 5-methoxyuridine-2',3',5'-tri-O-benzoate.

EXAMPLE 11

11 mmoles of 2,4-bis(trimethylsilyloxy)-5,6-dimethylpyrimidine and 12 mmoles of (CH₃)₃SiO—SO₂CF₃, dissolved in absolute 1,2-dichloroethane, were added under argon to 5.04 g. (10 mmoles) of 1-O-acetyl-2,3,5-tri-O-benzoyl-β-D-ribofuranose in 75 ml. of 1,2-dichloroethane and agitated for 3.5 hours at room temperature. The mixture was worked up as described in Example 1, yielding from methylene chloride/hexane 4.8 g. (82.2%) of 5,6-dimethyluridine-2',3',5'-tri-O-benzoate.

EXAMPLE 12

Under argon, 11 mmoles of 2,4-bis(trimethylsilyloxy)-6-methylpyrimidine and 12 mmoles of (CH₃)₃SiO—SO₂CF₃ in absolute acetonitrile were added to a solution of 5.04 g. (10 mmoles) of 1-O-acetyl-2,3,5-tri-O-benzoyl-β-D-ribofuranose in 100 ml. of absolute acetonitrile at +4° C.; the mixture was gradually warmed up and stirred for 3 hours at room temperature and then worked up according to Example 1. Column chromatography with chloroform-isopropanol on silicagel resulted, from ethyl acetate/hexane, in 4.35 g. (75.9%) of 6-methyluridine-2',3',5'-tri-O-benzoate.

EXAMPLE 13

Analogously to Example 12, 5.04 g. (10 mmoles) of 1-O-acetyl-2,3,5-tri-O-benzoyl-β-D-ribofuranose, 11 mmoles of 1-(trimethylsilyloxy)-1,2,4-triazole, and 12 mmoles of (CH₃)₃SiO—SO₂CF₃ were reacted with one another and then worked up as set forth in Example 1, yielding 2.94 g. (57.2%) of 1-(1,2,4-triazolyl)-β-D-ribofuranoside-2',3',5'-tri-O-benzoate, m.p. 105°–106° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for preparing a nucleoside by catalytically condensing a silylated organic base convertible to a nucleoside with a 1-O-acyl, 1-O-alkyl or 1-halo derivative of a masked sugar convertible to a nucleoside to form a nucleoside of said base and said sugar, the improvement which comprises:
    employing a catalyst for said condensation consisting essentially of a trialkylsilyl ester of an esterifiable mineral acid or of a strong sulfonic acid, each alkyl being of 1–6 carbon atoms and said acid having a —H₀ constant of at least 12.00, whereby a nucleoside of said base is formed containing principally the β-derivative of said sugar.

2. A process according to claim 1, further comprising hydrolyzing residual catalyst in the resultant reaction mixture to form a corresponding salt and hexamethyldisiloxane and removing said hexamethyldisiloxane therefrom by evaporation.

3. A process according to claim 2, wherein hydrolysis is effected by shaking with bicarbonate solution and said evaporation is effected with evaporation of residual solvent.

4. A process according to claim 1, wherein said catalyst is a trimethylsilyl ester.

5. A process according to claim 1, wherein said catalyst is (CH₃)₃—SiO—ClO₃, (CH₃)₃—SiO—SO₂CF₃ or (CH₃)₃SiOSO₂F.

6. A process according to claim 1, wherein the silylated organic base is silylated uracil, cytosine, 6-azauracil, 2-thio-6-azauracil, thymine, N-acetyladenine, guanine, lumazine, imidazole, pyrazine, thiazole or triazole.

7. A process according to claim 1, wherein the masked sugar is fully masked ribose, deoxyribose, arabinose or glucose.

8. A process according to claim 6, wherein the masked sugar is fully masked ribose, deoxyribose, arabinose or glucose and said catalyst is a trimethylsilyl ester.

9. A process according to claim 8, wherein said catalyst is (CH₃)₃—SiO—ClO₃, (CH₃)₃—SiO—SO₂CF₃ or (CH₃)₃SiOSO₂F.

10. A process according to claim 9, further comprising hydrolyzing residual catalyst in the resultant reaction mixture to form a corresponding salt and hexamethyldisiloxane and removing said hexamethyldisiloxane therefrom by evaporation.

11. A process according to claim 10, wherein hydrolysis is effected by shaking with bicarbonate solution and said evaporation is effected with evaporation of residual solvent.

* * * * *